(12) United States Patent
Fine

(10) Patent No.: US 8,613,958 B2
(45) Date of Patent: Dec. 24, 2013

(54) NITRIC OXIDE THERAPIES

(75) Inventor: David H. Fine, Cocoa Beach, FL (US)

(73) Assignee: GENO LLC, Cocoa, FL (US)

( * ) Notice: Subject to any disclaimer, the term of this patent is extended or adjusted under 35 U.S.C. 154(b) by 0 days.

(21) Appl. No.: 12/819,670

(22) Filed: Jun. 21, 2010

(65) Prior Publication Data

US 2010/0323036 A1 Dec. 23, 2010

Related U.S. Application Data

(60) Provisional application No. 61/219,200, filed on Jun. 22, 2009.

(51) Int. Cl.
| | | |
|---|---|---|
| *A61K 33/00* | (2006.01) | |
| *A61M 15/00* | (2006.01) | |
| *A62B 7/10* | (2006.01) | |
| *A61M 16/10* | (2006.01) | |

(52) U.S. Cl.
USPC .................. 424/718; 128/202.26; 128/203.16

(58) Field of Classification Search
None
See application file for complete search history.

(56) References Cited

U.S. PATENT DOCUMENTS

| | | | |
|---|---|---|---|
| 5,405,919 A | | 4/1995 | Keefer et al. |
| 6,841,166 B1 * | | 1/2005 | Zhang et al. .................. 424/443 |
| 2004/0131703 A1 | | 7/2004 | Bach et al. |
| 2006/0180147 A1 | | 8/2006 | Rounbehler et al. |
| 2006/0269620 A1 | | 11/2006 | Morris et al. |
| 2007/0087025 A1 | | 4/2007 | Fitzhuh et al. |
| 2007/0154570 A1 | | 7/2007 | Miller et al. |
| 2007/0235029 A1 * | | 10/2007 | Zhu et al. .................. 128/203.12 |
| 2008/0207713 A1 | | 8/2008 | Wang et al. |
| 2009/0214618 A1 * | | 8/2009 | Schoenfisch et al. ......... 424/426 |

FOREIGN PATENT DOCUMENTS

| | | | | |
|---|---|---|---|---|
| WO | WO 2008118360 | * | 10/2008 | ............ A61M 15/00 |
| WO | WO 2009/097343 | | 8/2009 | |
| WO | WO 2010/021942 | | 2/2010 | |

OTHER PUBLICATIONS

Dong (Derwent-Acc-No. 2007-664612 abstracting CN 1923308 published Mar. 7, 2007) 2 pages.*
Zhang et al. (JACS 2003, 125, 5015-5024).*
Lindberg et al. (British Journal of Anaesthesia 1998, 80: 213-217).*
Dong (Derwent-acc-No. 2007-664612 abstracting CN 1923308 published Mar. 7, 2007; 3 pages.*
Wang et al. Chemical Reviews 2002, 102(4), pp. 1091-1134).*
Rouadi et al. (J Appl Physiol 1999, 87, 400-406).*
Figure from Dong (Derwent-Acc-No. 2007-664612 abstracting CN 1923308; 3/7/7; 1 page.*
Zhang et al., "Nitric Oxide-Releasing Fumed Silica Particles: Synthesis, Characterization, and Biomedical Application," *J. Am. Chem. Soc.*, vol. 125, p. 5015-5024 (2003).
International Preliminary Report on Patent Ability for PCT/US2010/039320 dated Jan. 12, 2012.
European supplementary search report for European Application No. 10792554.7 dated Nov. 7, 2012.

\* cited by examiner

*Primary Examiner* — Ernst Arnold
(74) *Attorney, Agent, or Firm* — Steptoe & Johnson LLP

(57) ABSTRACT

A method for delivering nitric oxide therapy to a subject can include administering a composition including a nitric-oxide releasing agent and silica to the subject and releasing a therapeutic amount of nitric oxide from the composition.

14 Claims, 5 Drawing Sheets

NITRIC OXIDE THERAPIES

CLAIM OF PRIORITY

This application claims the benefit of prior U.S. Provisional Application No. 61/219,200, filed on Jun. 22, 2009, which is incorporated by reference in its entirety.

TECHNICAL FIELD

This description relates to methods of treatment.

BACKGROUND

The inhalation or topical exposure of nitric oxide gas to a subject can be beneficial in promoting healing of a wound, preparing a wound bed for further recovery, reducing infection and inflammation, and treating pulmonary disorders. However, typical nitric oxide (NO) therapies include compositions that may be toxic to a subject and can be difficult to administer.

SUMMARY

In general, a method for delivering nitric oxide therapy to a subject an include administering a composition including a nitric-oxide releasing agent and silica to the subject and releasing a therapeutic amount of nitric oxide from the composition. In certain circumstances, silica gel can prevent toxic compounds from entering the subject. In other circumstances, the composition further includes an antioxidant. The antioxidant can be ascorbic acid, alpha tocopherol, or gamma tocopherol.

In certain circumstances the composition can be in the form of an ointment. In other circumstances, the composition can be incorporated into an adhesive strip. The adhesive strip can optionally include a foil backing to prevent nitric oxide from being released into an external environment. In some circumstances, the adhesive strip can have a calibrated scale on one surface thereof for accurate measurement of an ointment dosage.

In certain circumstances, a composition can be in the form of a gum or lozenge. In other circumstances, the composition can be incorporated into a gas delivery device such as an inhaler or nasal cartridge.

In some circumstances, a therapeutic amount of nitric oxide is at least 1 ppm, at least 100 ppm, at least 200, or at least 300 ppm.

A composition for delivering nitric oxide therapy to a subject can include silica and a nitric oxide-releasing agent. The agent can be a polymeric composition having a polymer and at least one nitric oxide releasing $N_2O_2^-$ functional group. The agent can also be selected from the group consisting of X─[N(O)NO] and [N(O)NO─]X.

A method for manufacturing a nitric oxide therapy to a subject can include incorporating a therapeutic amount of a nitric oxide-releasing agent into a silica composition into a delivery device. The delivery device can be an inhaler, an adhesive strip, an ointment, a gum, or a lozenge.

DETAILED DESCRIPTION

Various embodiments are directed to methods, compositions and devices for nitric oxide (NO) therapies. Generally, nitric oxide (NO) is topically applied, inhaled, or otherwise delivered to the individual's lungs. Providing a therapeutic dose of NO can provide several benefits including reducing microbial infection, reducing inflammation, regulating the formation of collagen, and treating pulmonary disorders. In addition, a therapeutic dose of NO can be used to supplement or minimize the need for oxygen therapy or rapid descent to lower elevations to treat symptoms of high-altitude sickness. A therapeutic dose of NO may be used without inducing toxicity to a subject. For example a concentration greater than 1 ppm, greater than 100 ppm, or greater than 200 ppm can be used.

Figure 1:
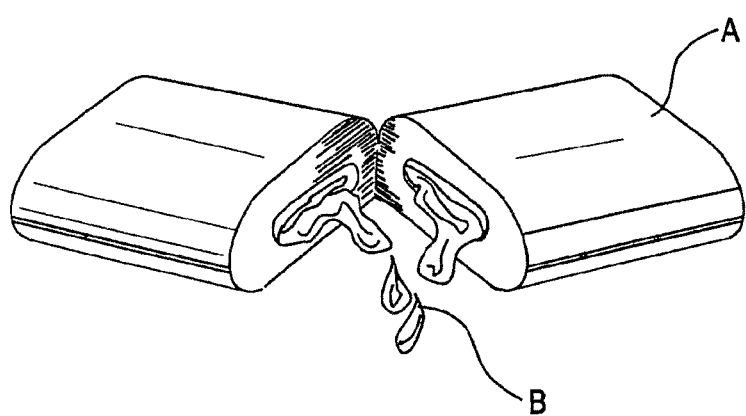
FIG. 1 illustrates a gum or lozenge containing a composition a nitric-oxide releasing agent and silica.

FIG. 1 illustrates a shell A, such as a gum or lozenge, the shell containing a therapeutic amount of a composition B, wherein the composition a nitric-oxide releasing agent and silica. The composition can be contained in the shell as shown, or alternatively, incorporated into the shell itself.

Figure 1A:
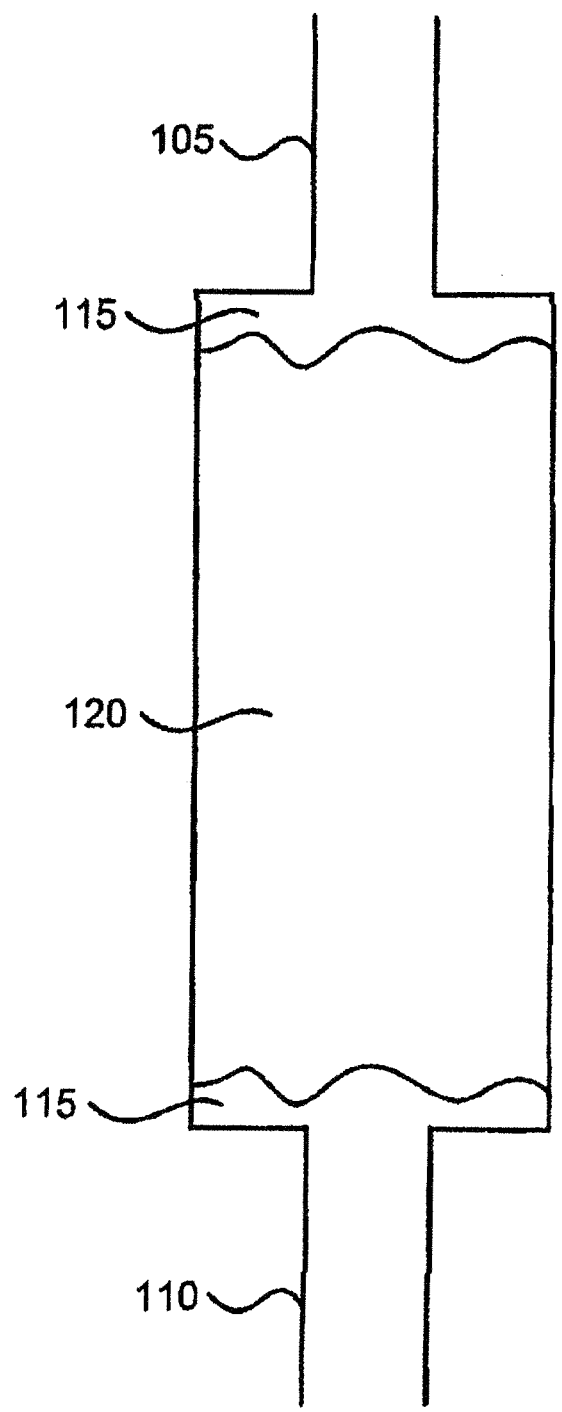
FIG. 1A illustrates one embodiment of a conversion cartridge 104 that generates NO from $NO_2$.

FIG. 1A illustrates one embodiment of a conversion cartridge 104 that generates NO from $NO_2$. The conversion cartridge 104 also may be referred to as a NO generation cartridge, a GENO cartridge, or a GENO cylinder. The conversion cartridge 104 includes an inlet 105 and an outlet 110. In one embodiment a particle filter 115 are located at both the inlet 105 and the outlet 110, and the remainder of the cartridge 104 is filled with a surface-active material 120 that is soaked with a saturated solution of antioxidant in water to coat the surface-active material. In another embodiment, the particulate filter 115 may be in the form of two concentric annular filters with the surface-active material 120 placed between the two annular filters. In this embodiment the gas flows from the inside of the annulus to the outside, or vice versa. In another embodiment, the surface-active material 120 and the filter material 115 are cast into one solid matrix as a sintered tube. In the example of FIG. 1A, the antioxidant is ascorbic acid.

Figure 2:
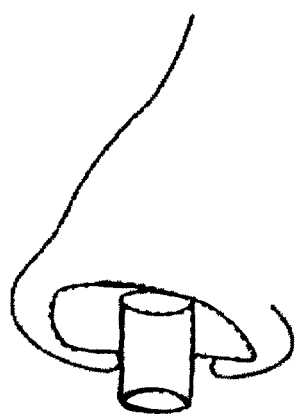
FIGS. 2 and 3 illustrate an inhaler or nasal plug that contains a nitric-oxide releasing agent and silica.
Figure 3:
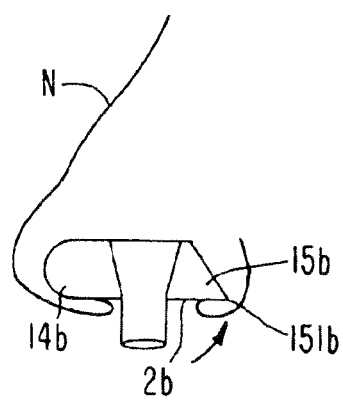

FIGS. 2 and 3 illustrate an inhaler or nasal plug that contains a nitric-oxide releasing agent and silica. The composition can be contained in the inhaler or nasal plug, or alternatively, incorporated into the inhaler or nasal plug itself.

Figure 4:
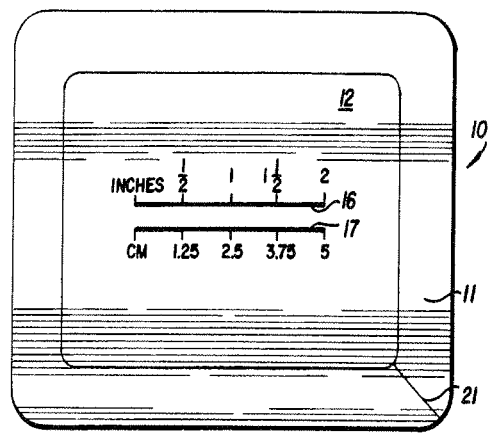
FIG. 4 illustrates an adhesive strip containing composition that includes a nitric-oxide releasing agent and silica.

FIG. 4 illustrates an adhesive strip 10 containing composition that includes a nitric-oxide releasing agent and silica. The composition can be an ointment or salve embedded into a pocket 12 on a surface 11 of the adhesive strip. The adhesive strip can include calibrations 16 and 17 that can be used to select or indicate the amount of ointment administered. The pocket can be a distance 21 from the perimeter of the adhesive strip.

Figure 5:
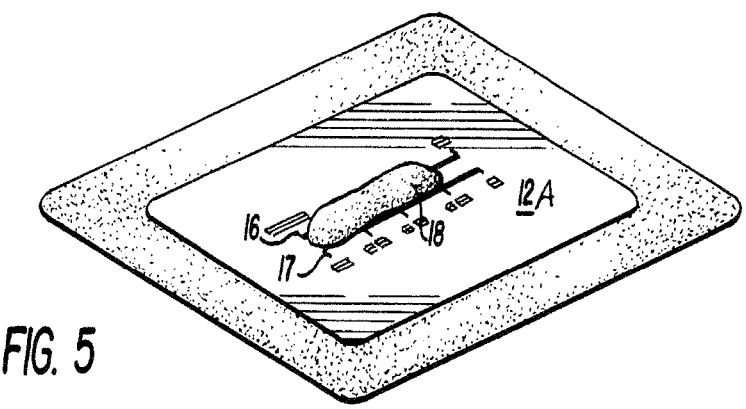
FIG. 5 illustrates an adhesive strip containing composition that includes a nitric-oxide releasing agent and silica.

FIG. 5 illustrates an adhesive strip wherein a composition such as an ointment or salve is embedded into a pocket 12 of the adhesive strip, the adhesive strip having calibrations 16 and 17 that can be used to select or indicate the amount of ointment 18 administered. The adhesive strip can include a foil backing 12A, that can prevent NO or $NO_2$ from being released into an external environment.

NO can be created from different processes and releasing compositions that are discussed, for example in U.S. patent application Ser. No. 11/206,305, which is incorporated by reference herein. Referring to FIG. 1A, in a general process for converting $NO_2$ to NO, an air flow having $NO_2$ is received through the inlet 105 and the air flow is fluidly communicated to the outlet 110 through the surface-active material 120 coated with the aqueous antioxidant. As long as the surface-active material remains moist and the antioxidant has not been used up in the conversion, the general process is effective at converting $NO_2$ to NO at ambient temperatures.

The inlet 105 may receive the air flow having $NO_2$, for example, from a pressurized bottle of $NO_2$, which also may be referred to as a tank of $NO_2$. The inlet 105 also may receive an air flow with $NO_2$ in nitrogen ($N_2$), air, or oxygen ($O_2$). The inlet 105 may also receive the air flow having $NO_2$ from an air pump that fluidly communicates an air flow over a permeation tube 235 containing liquid $N_2O_4$. The conversion occurs over a wide concentration range. Experiments have been carried out at concentrations in air of from about 0.2 ppm $NO_2$ to about 100 ppm $NO_2$, and even to over 1000 ppm $NO_2$.

In one example, a cartridge that was approximately 5 inches long and had a diameter of 0.8-inches was packed with silica gel that had first been soaked in a saturated aqueous solution of ascorbic acid. Other sizes of the cartridge are also possible. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other similar sizes of silica gel also are effective, provided that the particle size and the pore size within the particles are similar.

The silica gel was moistened with a saturated solution of ascorbic acid that had been prepared by mixing up to 35% by weight ascorbic acid in water, stirring, and straining the water/ascorbic acid mixture through the silica gel, followed by draining. It has been found that the conversion of $NO_2$ to NO proceeds well when the silica gel coated with ascorbic acid is moist. The conversion of $NO_2$ to NO does not proceed well in an aqueous solution of ascorbic acid alone.

The cartridge filled with the wet silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to 5,000 ml per minute. Using an annular cartridge, flow rates of up to 60,000 ml per minute have been used. The reaction also proceeds using other common antioxidants, such as variants of vitamin E (e.g., alpha tocopherol and gamma tocopherol).

The antioxidant/surface-active material GENO cartridge may be used for various therapies. In one such example, the GENO cartridge may be used as a $NO_2$ scrubber for NO inhalation therapy that delivers NO from a pressurized bottle source. The GENO cartridge not only scrubs the $NO_2$ but converts the $NO_2$ back into NO gas, which is then inhaled by the patient. This cartridge is also referred to as a recuperator. This GENO cartridge may be used to help ensure that no harmful levels of $NO_2$ are inadvertently inhaled by the patient. Additionally, the GENO cartridge ensures that the patient is receiving the entire NO dose as NO gas and not as the toxic form, $NO_2$.

According to one embodiment, a therapeutic composition is a mixture of a surface-activated material such as, but not limited to, silica gel and one or more suitable thermoplastic resins that are sintered at high temperatures to form a porous solid matrix. The polymers include, but are not limited to, polyethylene, polypropylene or any thermoplastic resin that can be ground into a fine powder and the poured into a mold and sintered at high temperature to form a porous solid matrix. The thermoplastic resin, when cured, provides a rigid porous structure with the surface-activated material embedded in the pores. Additionally, the polymer may be shaped or molded into any form.

According to one embodiment, the porous solid matrix is composed of at least 20% silica gel. In another embodiment, the porous solid matrix includes approximately 20% to approximately 60% silica gel. In yet another embodiment, the porous solid matrix is composed of 50% silica gel. As those skilled in the art will appreciate, any ratio of silica gel to thermoplastic resin is contemplated so long as the mechanical and structural strength of the porous solid matrix is maintained. In one embodiment, the densities of the silica gel and the polymer are generally similar in order to achieve a uniform mixture and, ultimately, a uniform porous solid matrix.

According to one method, the solid matrix is formed by mixing silica gel with a thermoplastic resin. The mixture is then sintered at a high temperature to form a porous solid matrix and allowed to cool. After the porous solid matrix is formed, the porous solid matrix is flushed with an antioxidant solution. In one embodiment, the antioxidant solution is approximately 20% ascorbic acid in water. Alternatively, ascorbic acid may be substituted with other antioxidants such as, but not limited to, alpha tocopherol or gamma tocopherol. In other embodiments, the antioxidant solution may have varying antioxidant concentrations. Dissolved gases (e.g., oxygen and air) are excluded from the antioxidant solution in order to prevent the formation of microscopic gas bubbles around the solid polymer/silica gel matrix. The gas bubbles would alter the surface chemistry and would prevent $NO_2$ from interacting with the antioxidant liquid inside the silica gel.

Once the solid matrix has been flushed, the excess antioxidant solution that is not bound by the silica gel may be rinsed off in order to minimize the precipitation of excess antioxidant solution during the drying step. According to one embodiment, the porous solid matrix is vacuum dried until the moisture content is reduced to approximately 30%. In alternate embodiments, the solid matrix may be dried to have any moisture content ranging from approximately 1% to approximately 99%. During the drying process, precautions need to be taken to ensure that oxygen is excluded. The dried, solid matrix is assembled into the body and flushed with inert gas before and during the sealing process. Oxygen is excluded from the manufacturing process and during storage in order to prevent the ascorbic acid (or other antioxidants) from slowly oxidizing to dehydro-ascorbic acid and other oxidation products during long-term storage. In another embodiment, the cartridge is dried until there is no detectable water present, and the cartridge is then sealed and packaged dry in a moisture-proof container. The dried cartridge is reconstituted into an active cartridge by exposing the cartridge to water prior to use.

Compositions capable of releasing NO are taught, for example in U.S. Pat. Nos. 7,425,218; 6,397,660; 6,200,558; 5,632,981; 5,525,357; and 5,405,919, which are incorporated by reference herein.

NO can be released from certain devices, such as those taught in U.S. Application No. 61/090,617, which is incorporated by reference herein. For example, a light, portable device for delivering NO with air has the potential to improve a patient's quality of life. The device may be powered by a small, battery-driven pump or by patient inhalation (using an inhaler used in a manner similar to smoking a cigar). Additionally, a treatment providing NO (e.g., converting $N_2O_4$ into NO) would be more cost effective than oxygen therapy.

Currently, approved devices and methods for delivering inhaled NO gas require complex and heavy equipment. NO gas is stored in heavy gas bottles with nitrogen and no traces of oxygen. The NO gas is mixed with air or oxygen with specialized injectors and complex ventilators, and the mixing process is monitored with equipment having sensitive microprocessors and electronics. All this equipment is required in order to ensure that NO is not oxidized into nitrogen dioxide ($NO_2$) during the mixing process since $NO_2$ is highly toxic. However, this equipment is not conducive to use in a non-medical facility setting (e.g., combat operations or remote wilderness) since the size, cost, complexity, and safety issues restrict the operation of this equipment to highly-trained professionals in a medical facility.

In contrast, the delivery devices disclosed herein are self-contained, portable systems that do not require heavy gas bottles, sophisticated electronics, or monitoring equipment. Additionally, the delivery devices are easy to use and do not require any specialized training. Moreover, the delivery devices allow an individual to self-administer a NO treatment. The delivery devices are also lightweight, compact, and portable. According to one embodiment, the NO delivery device is the size of a cigar or a conventional inhaler for one-time use or short-term treatments. Alternatively, the NO delivery device is a larger device, yet portable device that can deliver NO for longer periods of time.

Useful pharmacological agents can be provided by incorporating nitric oxide-releasing $N_2O_2$-functional groups into a biopolymer. Accordingly, the $N_2O_2$-functional group is "bound to the polymer" as that term has been defined herein. The term NONOate is used herein as a shorthand to refer to the nitric oxide-releasing $N_2O_2$-group. It has been discovered that incorporation of a NONOate into a biopolymer provides a biopolymer-bound NONOate composition that can be applied with specificity to a biological site of interest. Site specific application of the biopolymer-bound NONOate enhances the selectivity of action of the nitric oxide-releasing NONOate. If $N_2O_2$ functional groups attached to the biopolymer are necessarily localized, then the effect of their nitric oxide release will be concentrated in the tissues with which they are in contact. If the biopolymer is soluble, selectivity of action can still be arranged, for example, by attachment to or derivatization of an antibody specific to the target tissue. Similarly, attachment of $N_2O_2$ groups to small peptides that mimic the recognition sequences of ligands for important receptors provides localized concentrated effect of nitric oxide release, as would attachment to oligonucleotides capable of site-specific interactions with target sequences in a nucleic acid. Other proteins, peptides, polypeptides, nucleic acids and polysaccharides, including hormones and motility, chemotactic and extravasating factors or agents, can be similarly utilized.

By way of illustration, a piperazine monoNONOate derivative can be covalently attached to a polypeptide containing the IKVAV recognition sequence important in tumor cell chemotaxis. Through retention of both the capacity to regenerate NO as an antichemotactic agent and the affinity of the IKVAV sequence for tumor cells and/or sites in the vascular and lymphatic systems where the tumor cells tend to attach, metastasis can be reduced or even prevented.

It is believed that longevity of nitric oxide release in the biopolymer-bound NONOate compositions of the present invention is to be attributed both to the physical structure of the composition and to electrostatic effects. Thus, it is believed that if the biopolymer is an insoluble solid, $N_2O_2$-groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2$-functional group also tends to increase the half-life of nitric oxide generation. The mechanism of this rate retardation may be attributable simply to repulsive electrostatic interactions, i.e., increasing the number of $H^+$ positive charges in the vicinity of the $N_2O_2$-groups inhibits attack of positively charged $H^+$ ions on the $N_2O_2$-functional group and slows the rate of its $H^+$ catalyzed decomposition. For example, by attaching amino groups to the polymeric support that are capable of forming the nitric oxide-releasing $N_2O_2$-functional group on reaction with nitric oxide, partially converted structures can be produced on less-than-exhaustive treatment with nitric oxide that after exposure to water contain a large number of positively charged ammonium centers surrounding the $N_2O_2$-group that electrostatically inhibit the approach of $H^+$ ions capable of initiating nitric oxide loss from the nitric oxide-releasing $N_2O_2$-functional group.

The nitric oxide-releasing $N_2O_2$-functional groups that are bound to the biopolymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide-releasing X[N(O)NO] group in the vicinity of the particular cells of interest. As an example, covalent attachment of a protecting group to the anionic [N(O)NO]-function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/nucleophile complex can be targeted to maximize the desired effect. While the biopolymer-bound NONOate compositions of the present invention are capable of releasing nitric oxide in an aqueous solution, such a compound preferably releases nitric oxide under physiological conditions.

For example, a NONOate functionality can be attached to a tumor-specific antibody or other protein which has one or more lysine side chain amino groups that are unnecessary to the function of the protein by reacting said lysine group(s) with a derivatizing agent capable of covalently attaching first to the lysine amino nitrogen then in a subsequent step to the sulfur atom of an O-functionalized NONOate containing a free thiol grouping elsewhere in the molecule. Once such a protein arrives at the desired target tissue after systemic application, enzymatic or hydrolytic removal of the substituent bound to oxygen frees the anionic NONOate function to concentrate NO release at that site.

The preferred nitric oxide-releasing $N_2O_2$-functional group which is used to form the biopolymer-bound NONOates of the present invention is defined by the formula:

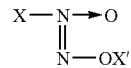

wherein X is an organic or inorganic moiety and X' is an organic or inorganic substituent, a pharmaceutically acceptable metal center, a pharmaceutically acceptable cation, or the like. The $N_2O_2^-$ group is bonded to the biopolymer through either or both the linking groups X and X'. The nitric oxide-releasing $N_2O_2$-functional group is preferably a nitric oxide/nucleophile adduct, e.g., a complex of nitric oxide and a nucleophile most preferably a nitric oxide/nucleophile complex which contains the anionic moiety $X[N(O)NO]^-$, where X is any suitable nucleophile residue. The nucleophile residue is preferably that of a primary amine (e.g., $X=(CH_3)_2CHNH$, as in $(CH_3)_2CHNH[N(O)NO]Na$), a secondary amine (e.g., $X=(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, X=2-(ethylamino)ethylamine, as in the zwitterion $CH_3CH_2N[N(O)NO]^-CH_2CH_2NH_3^+$, or X=3-(n-propylamino)propylamine, as in the zwitterion $CH_3CH_2CH_2N[N(O)NO]^-CH_2CH_2CH_2NH_3^+$), or oxide (i.e., $X=O^-$, as in $NaO[N(O)NO]Na$), or a derivative thereof. Such nitric oxide/nucleophile complexes are capable of delivering nitric oxide in a biologically usable form as a predictable rate.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed is:

1. A method for delivering nitric oxide therapy to a subject comprising:
    exposing a composition including a nitric-oxide releasing agent, silica, and an antioxidant to water in a chamber of a gas delivery device that includes an inlet, an outlet, a particle filter at the outlet, and the chamber,
    wherein the nitric-oxide releasing agent is polymeric composition including a polymer and at least one nitric oxide releasing $N_2O_2^-$ functional group,
    administering the gas delivery device to the subject;
    generating an air flow through the inlet, the composition in the chamber, and the outlet by subject inhalation; and
    releasing a therapeutic amount of nitric oxide from the composition into the air flow.

2. The method of claim 1, wherein the silica prevents toxic compounds from entering the subject.

3. The method of claim 2, wherein the antioxidant is ascorbic acid, alpha tocopherol, or gamma tocopherol.

4. The method of claim 1, wherein the composition is an ointment.

5. The method of claim 1, wherein the composition is incorporated into an adhesive strip.

6. The method of claim 5, wherein the adhesive strip has a calibrated scale on one surface thereof for accurate measurement of an ointment dosage.

7. The method of claim 1, wherein the composition is in the form of a gum or lozenge.

8. The method of claim 1, wherein the delivery device is an inhaler or nasal cartridge.

9. The method of claim 1, further comprising a foil backing.

10. The method of claim 5, wherein the foil backing prevents nitric oxide from being released into an external environment.

11. The method of claim 1, wherein the therapeutic amount of nitric oxide is at least 1 ppm.

12. The method of claim 1, wherein the therapeutic amount of nitric oxide is at least 100 ppm.

13. The method of claim 1, wherein the therapeutic amount of nitric oxide is at least 200 ppm.

14. The method of claim 1, wherein the therapeutic amount of nitric oxide is at least 300 ppm.

* * * * *